United States Patent [19]

Hijikata

[11] 4,248,536

[45] Feb. 3, 1981

[54] DUAL WAVELENGTH PHOTOMETRIC DEVICE

[75] Inventor: Kazuo Hijikata, Hachioji, Japan

[73] Assignee: Olympus Optical Company Limited, Tokyo, Japan

[21] Appl. No.: 49,164

[22] Filed: Jun. 18, 1979

Related U.S. Application Data

[63] Continuation of Ser. No. 897,367, Apr. 18, 1978, abandoned.

[30] Foreign Application Priority Data

Apr. 20, 1977 [JP] Japan ................................. 52-45432

[51] Int. Cl.$^3$ ......................... G01J 3/50; G01N 21/27
[52] U.S. Cl. ..................................... 356/416; 356/434
[58] Field of Search ............... 356/320, 409, 410, 414, 356/416, 418, 419, 425, 433, 434, 435–439; 250/339, 343, 345

[56] References Cited

U.S. PATENT DOCUMENTS

| | | | |
|---|---|---|---|
| 3,089,382 | 5/1963 | Hecht et al. | 356/410 |
| 3,805,074 | 4/1974 | McCormack | 250/339 X |
| 3,887,281 | 6/1975 | Kurita et al. | 356/419 |

*Primary Examiner*—F. L. Evans
*Attorney, Agent, or Firm*—Toren, McGeady and Stanger

[57] ABSTRACT

A photometric device comprises a photometric optical system for obtaining light outputs each having a predetermined wavelength by transmitting light from a light source to a sample to be measured through different light paths each having a filter, a detector for converting each light output into an electric signal, a switch for deriving first electric signals for one predetermined wavelength and second electric signals for another predetermined wavelength from the output signals of the detector, and a signal treating circuit for treating the first and the second electric signals to obtain a light absorption amount of the sample.

2 Claims, 14 Drawing Figures

0 Level

0 Level

DUAL WAVELENGTH PHOTOMETRIC DEVICE

This is a continuation of application Ser. No. 897,367, filed Apr. 18, 1978, now abandoned.

BACKGROUND OF THE INVENTION

1. Field of the Invention

The present invention relates to a photometric device for improving performance by removing each kind of noises.

2. Description of the Prior Art

There is utilized a two-wavelength photometry for lessening an influence of absorption, scattering or the like caused by scratches or stains of a detector such as a photometric cell or foreign matters or the like in a solution to be detected in quantitative analysis by a colorimetric method. The two-wavelength photometry uses two different kinds of wavelengths such as a maximum sample absorption wavelength $\lambda_1$ and a less sample absorption wavelength $\lambda_2$, and as a light absorption amount of an actual sample, a light absorption amount in case of the wavelength $\lambda_2$ is substracted from a light absorption amount in case of the wavelength $\lambda_1$, a difference between both is sought and a light absorption amount in the wavelength $\lambda_1$ of the actual sample is obtained.

FIG. 1a shows one embodiment of an output waveform in case of receiving two lights of a wavelength $\lambda_1$ and a wavelength $\lambda_2$ by a single detector in a photometric device by such two wavelength method, wherein the portion of the wavelength $\lambda_1$ and the portion of the wavelength $\lambda_2$ alternately appear at suitable intervals.

With the use of a wavelength discriminating signal shown in FIG. 1b, discrimination of the wavelength is carried out by a circuit having a construction shown in FIG. 2. In FIG. 2, reference numeral 1 is a detector, reference numeral 2 is a discriminating signal generating circuit, and a switch 3 is switched by an output signal of the circuit 2 so as to obtain two outputs. That is, in case of closing a contact 3a of the switch 3, the output for the wavelength $\lambda_1$ shown in FIG. 1c is obtained, while in case of closing a contact 3b of the switch 3, the output for the wavelength $\lambda_2$ in FIG. 1d is obtained.

These signals contain a shadowed portion which does not vary by the amplitude of a photometric signal. When this shadowed portion is existent, even if the amplitudes of the photometric signals for the wavelengths $\lambda_1$ and $\lambda_2$ are varied at the same ratio, a ratio $\lambda_1/\lambda_2$ thereof cannot be kept constantly and as a result, linearity of characteristic as a whole of the photometric device is deteriorated.

The cause of the shadowed portion is due to stray light of the optical system or dark current of the detector. There is also a method of removing the shadowed portion with the use of a preamplifier instead of direct wavelength discrimination of the detector output, but in this case, a temperature drift of an amplifier circuit or a shift of offset adjustment becomes a problem. Further, the dark current of the detector and the stray light are influenced by the surroundings and are not always certain. There is further a method of discriminating a wavelength by sampling and holding a point X and a point Y of FIG. 1a, but in this case, the above-described disadvantage cannot be avoided.

SUMMARY OF THE INVENTION

An object of the present invention is to eliminate the above disadvantages of the conventional method.

Another object of the present invention is to provide a photometric device for carrying out photometry with high performance by removing each kind of noises caused by the dark current of the detector, the drift of the amplifier, the stray light of the optical system or the like.

According to the present invention, a photometric device comprises a photometric optical system for obtaining light outputs each having a predetermined wavelength by transmitting light from a light source to a sample to be measured through different light paths each having a filter, a detector for converting each light output into an electric signal, a switch for deriving first electric signals for one predetermined wavelength and second electric signals for another predetermined wavelength from the output signals of the detector, and a signal treating circuit for treating the first and the second electric signals to obtain a light absorption amount of the sample. One of the light paths comprises a rotating mirror, reflecting mirrors, a first filter for transmitting a first predetermined wavelength and a half-mirror and the other of the light paths comprises the rotating mirror, a second filter for transmitting a second predetermined wavelength, and the half-mirror. The signal treating circuit comprises two signal paths and a differential circuit for obtaining a difference between the outputs of both signal paths. Each signal path comprises a sample and hold circuit for maintaining the level of the signal supplied thereto, a high-pass filter, a rectifying circuit, a low-pass filter, a zero adjusting circuit and a logarithmic converting circuit which are arranged in a described order.

DESCRIPTION OF THE PREFERRED EMBODIMENT

Figure 1A:
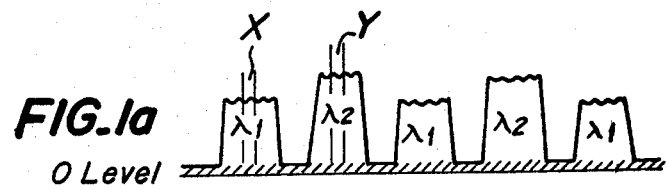
FIGS. 1a–1d are waveform charts showing the operation of a prior photometric device by a two wavelength photometry.
Figure 1B:
Figure 1C:
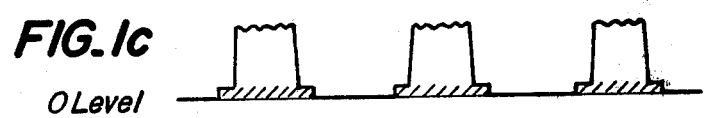
Figure 1D:
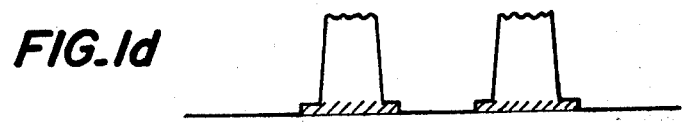
Figure 2:
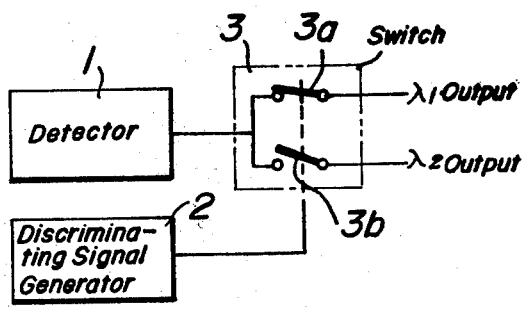
FIG. 2 is a block diagram showing a wavelength discriminating circuit of the same device.
Figure 3:
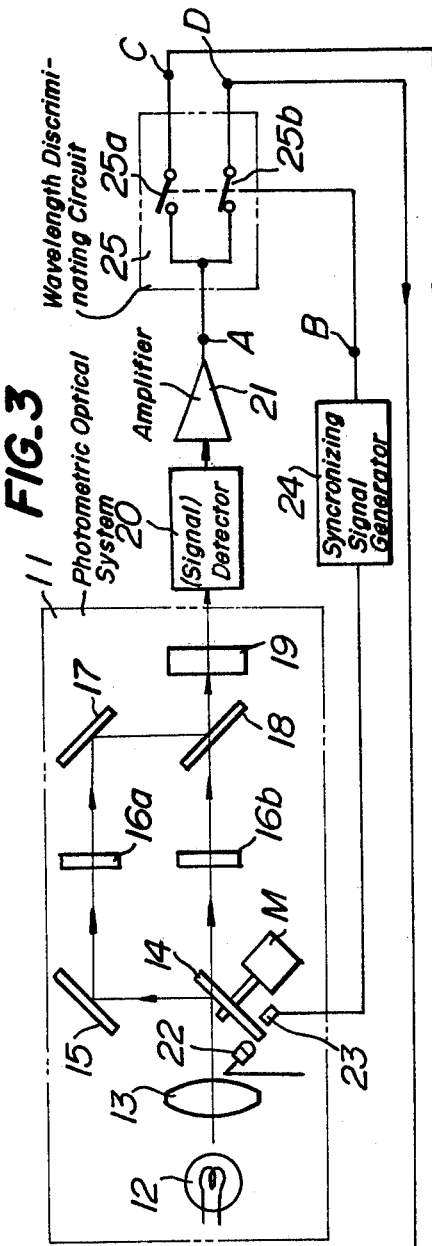
FIG. 3 is a block diagram showing one embodiment of a photometric device by a two wavelength photometry according to the present invention.
Figure 3:
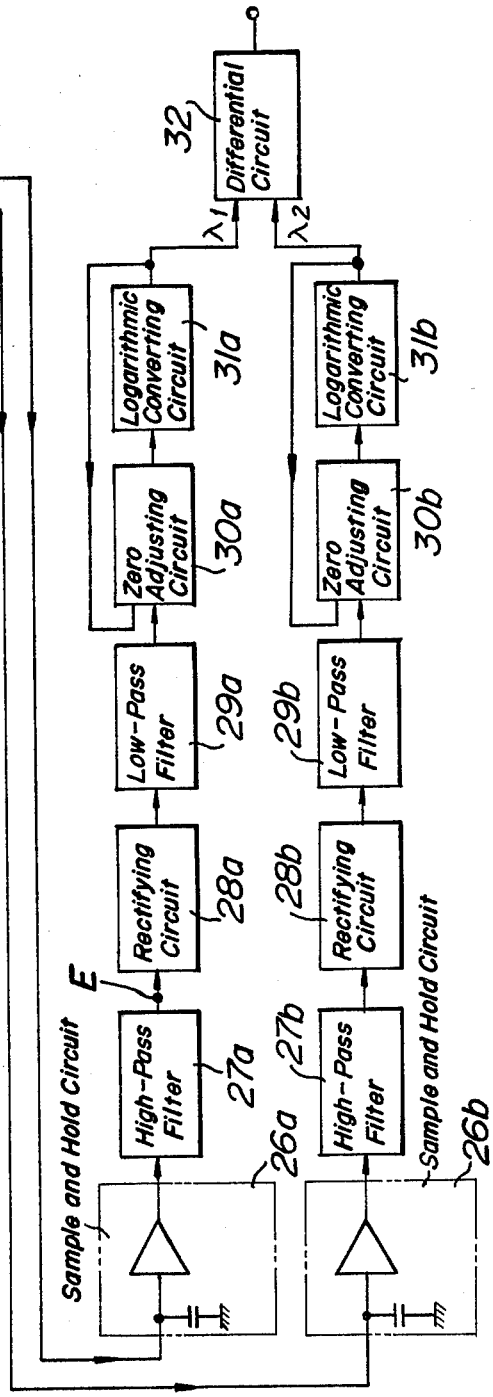

Referring now to FIGS. 3 and 4 one embodiment of a photometric device according to the present invention is shown. In a photometric optical system 11 shown in FIG. 3, the light transmitted from a light source 12 is reflected by a rotating mirror 14 through a lens 13 and enters into a sample 19 through a reflecting mirror 15, a first filter 16a for transmitting a wavelength $\lambda_1$, a reflecting mirror 17 and a half-mirror 18.

The light from a light source 2 on the other hand transmits the position of the rotating mirror 14 and enters into the sample 19 through a second filter 16b for transmitting a wavelength $\lambda_2$ and the half-mirror 18. The rotating mirror 14 comprises the portions for reflecting the light and the portions for transmitting the light which are arranged alternately and obtains two light outputs for the wavelengths $\lambda_1$ and $\lambda_2$ passed through the sample 19 through two light paths inclusive of the first filter 16a and the second filter 16b.

A single detector 20 receives these light outputs, converts them into electric signals and amplifiers them by an amplifier 21. A signal at the output terminal A of the amplifier 21 has a waveform shown in FIG. 4a.

A light source 22 and a light receiving element 23 are opposed to each other by sandwiching the rotating mirror 14, thereby obtaining a wavelength discriminating signal. With this signal a synchronizing signal generator 24 generates a synchronizing signal shown in FIG. 4h.

There is provided a wavelength discriminating circuit 25 for discriminating signals for two wavelengths $\lambda_1$ and $\lambda_2$ from the signals at the output terminal of the amplifier 21. The wavelength discriminating circuit 25 comprises a normally off contact 25a and a normally on contact 25b, and these contacts are driven by the synchronizing signal. The normally off contact 25a is closed under the H(high) level of the synchronizing signal, and opened under the L(low) level of the synchronizing signal. The normally on contact 25b is operated adversely thereto. Accordingly, a signal at the output terminal C of the wavelength discriminating circuit 25 has a waveform shown in FIG. 4C and a signal at the other output terminal D has that shown in FIG. 4d.

A sample and hold circuit 26a consists of a capacitor and an amplifier, and when the normally off contact 25a is closed, a signal is output as it is, and when the contact 25a is opened, a signal level at the instant of opening the path is maintained.

Figure 4A:
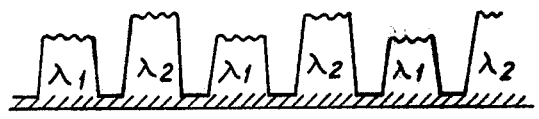
FIGS. 4a–4e are waveform charts showing the operation of the device shown in FIG. 3.
Figure 4B:
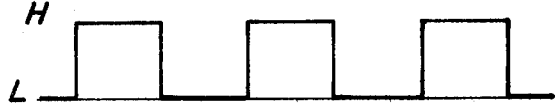
Figure 4C:
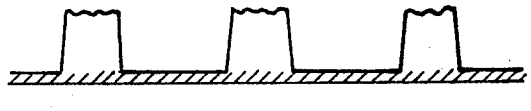
Figure 4D:
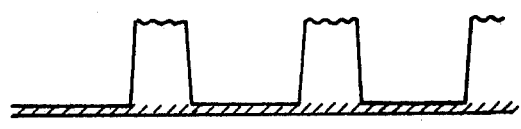
Figure 4E:
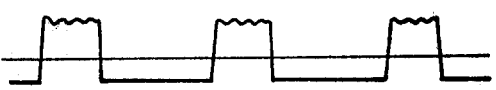

A high-pass filter 27a connected to the sample and hold circuit 26a receives this signal and generates the output having a waveform shown in FIG. 4e.

Figure 5:
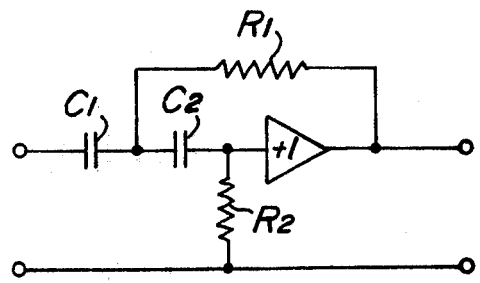
FIG. 5 is a circuit diagram showing one embodiment of a bypass filter used in the device according to the present invention.

When a cycle of the light signals alternately output by the photometric optical system 11 and a cutoff frequency of the high-pass filter 27a are properly selected, the effects caused by not only the stray light generated in the optical system 11, the dark current of the detector 20 and the drift and offset shift of the amplifier but also the hum noise superimposed on the signal can be eliminated. Therefore, various factors for lowering these photometric performances are removed and an excellent photometric device having linearity can be realized without receiving any surrounding influence. FIG. 5 shows one embodiment of the construction of the high-pass filter 27a in detail.

In the embodiment shown in FIG. 3, the high-pass filter 27a is cascade connected to a rectifying circuit 28a, a low-pass filter 29a, a zero adjusting circuit 30a and a logarithmic converting circuit 31a, while the normally on contact 25b is cascade connected to a sample and hold circuit 26b, a high-pass filter 27b, a rectifying circuit 28b, a low-pass filter 29b, a zero adjusting circuit 30b and a logarithmic converting circuit 31b, and at a differential circuit 32 is taken a difference between the outputs of both the logarithmic converting circuits 31a and 31b and then a signal treatment of two wavelength photometry is carried out and as a result, a light absorption amount in the wavelength $\lambda_1$ of the sample 19 can be obtained.

The zero adjusting circuits 30a, 30b serve as a circuit for correcting zero point of the measuring circuit by a standard material having the known concentration before measuring the concentration of an unknown material.

The logarithmic converting circuits 31a, 31b serve as a circuit for converting transmissibility of the light of the sample into the absorbancy (optical concentration), and the light absorbancy is in a relation of log1/T when the transmissibility is T.

Figure 6:
FIGS. 6 and 7 are waveform charts showing other embodiments of a signal which can be treated by the embodiment of FIG. 4.
Figure 7:

As signals which can be treated in the two wavelength photometric device in this embodiment, it is preferable to use not only those in FIG. 4a but also those in FIG. 6 or 7.

In the illustrated embodiment, the wavelength discriminating circuit 25 is indicated as a mechanical switch for the sake of simplicity, but a stationary type such as a semiconductor switch is also usable.

The present invention is not limited to the above embodiments but can be modified within the range not departing from the essential scope of the invention.

For example, the above embodiment shows the case of two wavelength photometry, but the present invention can be applied to the case of multi-wavelength photometry by designing an optical system, a synchronizing signal generator and a wavelength discriminating circuit.

In FIG. 4, if the zero adjusting circuits 30a, 30b and the logarithmic converting circuits 31a, 31b are removed, the device can be applied to transmission photometry, and the invention can be utilized as an illuminometer of two wavelengths by designing an optical system.

As described above, according to the present invention, it is possible to provide a photometric device by removing each kind of noises caused by the stray light, the dark current of the detector, the drift of the amplifier or the like.

What is claimed is:

1. A photometric device comprising a photometric optical system for obtaining light outputs each having a predetermined wavelength by transmitting light from a light source to a sample to be measured through different light paths each having a filter, a detector for converting each light output into an electric signal, a switch for deriving first electric signals for one predetermined wavelength and second electric signals for another predetermined wavelength from the output signals of the detector, and a signal treating circuit for treating the first and the second electric signals to obtain a light absorption amount of the sample;

wherein one of the light paths comprises a rotating mirror, reflecting mirrors, a first filter for transmitting a first predetermined wavelength and a half-mirror and the other of the light paths comprises the rotating mirror, a second filter for transmitting a second predetermined wavelength and the half-mirror and wherein the signal treating circuit comprises two signal paths and a differential circuit for obtaining a difference between the outputs of both signal paths, each signal path including a sample and hold circuit for maintaining the level of the signal supplied thereto, a high-pass filter, a rectifying circuit and a low-pass filter arranged in a predetermined order, and wherein means are included for synchronizing said switch with the rotating mirror.

2. A photometric device as claimed in claim 1, wherein each signal path also includes a zero adjusting circuit and a logarithmic converting circuit.

* * * * *